United States Patent [19]
Culp

[11] Patent Number: 5,125,403
[45] Date of Patent: Jun. 30, 1992

[54] DEVICE AND METHOD FOR ENGAGEMENT OF AN OXIMETER PROBE

[76] Inventor: Joel B. Culp, 605 Pioneer Ave., Kent, Ohio 44240

[21] Appl. No.: 658,194

[22] Filed: Feb. 20, 1991

[51] Int. Cl.⁵ .............................................. A61B 5/00
[52] U.S. Cl. ..................................... 128/633; 128/665
[58] Field of Search ............... 128/632, 633, 637, 639, 128/640, 644, 664, 665, 666–667, 672, 687–689, 653 A, 653 R, 653 AF, 691–694, 680–682, 685–686

[56] References Cited

U.S. PATENT DOCUMENTS

| | | | |
|---|---|---|---|
| 3,482,565 | 12/1969 | Gowen | 128/667 |
| 4,406,289 | 9/1983 | Wesseling et al. | 128/672 |
| 4,685,464 | 8/1987 | Goldberger et al. | 128/666 |
| 4,726,382 | 2/1988 | Boehmer et al. | 128/667 |
| 4,867,165 | 9/1989 | Noller et al. | 128/633 |
| 5,002,061 | 3/1991 | Close et al. | 128/687 |

OTHER PUBLICATIONS

W. E. Hammer et al.; Indirect Blood Pressure Finger Cuff; Sep. 4, 1965; p. 593; IBM Technical Disclosure Bulletin.
Ohmeda Division of The BOC Group Inc., Advertisement for Ohmeda Probes (1989).
Hewlett-Packard Company, Instructions for Model HP M1190A Reusable Finger Transducer.
Endless Possibilities, Inc., Advertisement for BOINKS! Brand Plastic Woven Tubes.
Published abstract for unissued U.S. Pat. No. 4,928,691, Offical Gazette, Dec. 1990.

*Primary Examiner*—Kyle L. Howell
*Assistant Examiner*—Jeffrey R. Jastrzab
*Attorney, Agent, or Firm*—Howard S. Robbins

[57] ABSTRACT

An electro-optical sensor probe (12) for non-invasive monitoring of blood oxygenation levels is engaged with the blood-perfused tissue (23) of a patient by a device (10) having a woven tube (20) that receives the probe (12) and selectively engages the probe (12) and the tissue (23). The tube (20) includes a cuff (27) formed integrally therewith for carrying the probe (12). Once the probe (12) located within cuff (27) is placed into engagement with tissue (23), tube (20) is extended over the tissue (23).

8 Claims, 2 Drawing Sheets

DEVICE AND METHOD FOR ENGAGEMENT OF AN OXIMETER PROBE

TECHNICAL FIELD

The present invention relates generally to devices for measurement of the degree of oxygen saturation of the blood. More particularly, the present invention relates to photoelectric photometers known as oximeters which are used to measure the oxygenated fraction of the hemoglobin in blood which is circulating in a particular tissue of an animal or human, by observation of the absorption of light transmitted through or reflected from the blood. Still more specifically, the present invention relates to a device and method for attaching non-invasive oximeter sensor probes to a patient.

BACKGROUND ART

The level of blood oxygenation is of fundamental importance in establishing the health of both animals and humans. Often the successful analysis and treatment of a great many injuries and illnesses requires the constant surveillance of blood oxygenation level. One of the most popular and successful non-invasive techniques for measuring blood oxygenation levels is based on the knowledge that the magnitude of light passing through blood-perfused tissue is directly related to the level of blood oxygenation. Oximeters are devices that generate light in a non-invasive electro-optical sensor probe attached to a patient and measure light reflection or transmission during transillumination of the blood-perfused tissue of the patient's body part to which the sensor is attached.

Oximeter probes include a light source and photosensor in a malleable, flexible holder positioned in contact with the tissue at which the measurement is to be made, typically the thinnest available tissue section such as a fingertip, toe, hand or foot. In the past a variety of oximeter probes, both reusable and disposable, have been developed to allow engagement to these various body parts. However, these probes are cumbersome to attach, use and remove, are expensive, tend to break easily, do not accommodate a variety of appendage sizes, and allow enough probe movement with patient motion to introduce measurement errors called motion artifact errors.

One line of representative oximeter probes is made by Ohmeda of Louisville Colo. Ohmeda manufactures probes contained within a spring biased clip that is used to bias the probe into contact with a fingertip or toe. Other probes use elaborate patterns of tapes and adhesives to secure the probe to the tissue of interest. Hewlett-Packard Company of Palo Alto California manufactures the model HP M1190A Reusable Finger Transducer, a rubber capsule fitting over the fingertip.

Often times those patients whose conditions demand constant monitoring of blood oxygenation levels are the least able physically to withstand the rigors of presently employed sensor probe engagement devices and techniques. For example, burn and/or traumatized patients often cannot withstand the pressure of spring-biased clips on injured tissue, and find the time-consuming, laborious process of applying and removing securing tapes and adhesives excruciating at best and detrimental to their recovery. Occasionally the extreme pain of such a procedure to a patient may result in improper engagement of the probe by all but the most experienced health care professional. Moreover, as is often found in emergency situations, patients are diaphoretic or have oils or foreign substances on their tissue making it extremely difficult to use oximeter sensors secured by tape or adhesives.

SUMMARY OF THE INVENTION

It is, therefore, an object of the present invention to provide a device and method for engagement of a probe such as an oximeter probe with the tissue at which the measurement is to be made that is durable, inexpensive and able to accommodate a variety of tissue sizes and configurations.

It is another object of the present invention to provide a device and method for engagement of a probe such as an oximeter probe, as set forth above, that does not require tapes or adhesives.

It is still another object of the present invention to provide a device and method for engagement of a probe such as an oximeter probe, as set forth above, that is either disposable or reusable, and if reused or moved to another tissue location will engage just as effectively as if new.

It is yet another object of the present invention to provide a device and method for engagement of a probe such as an oximeter probe, as set forth above, that includes no springs or other significant pressure inducing elements, or breakable parts.

It is a further object of the present invention to provide a device and method for engagement of a probe such as an oximeter probe, as set forth above, that does not restrict blood flow, by allowing expansion with tissue swelling, and that minimizes tissue necrosis and facilitates rehabilitation by allowing substantial air flow around the tissue.

It is still a further object of the present invention to provide a device and method for engagement of a probe such as an oximeter probe, as set forth above, that minimizes allergic reaction, does not injure the tissue with which it is engaged, and may be sanitized for reuse.

It is yet a further object of the present invention to provide a device and method for engagement of a probe such as an oximeter probe, as set forth above, that would be easy to apply without great medical skill, thereby minimizing the possibility of incorrect engagement.

It is an additional object of the present invention to provide a device and method for engagement of a probe such as an oximeter probe, as set forth above, that would minimize so-called motion artifact errors.

These and other objects and advantages of the present invention over existing prior art forms will become more apparent and fully understood from the following description in conjunction with the accompanying drawings.

In general, a device for engaging a sensor probe with the tissue of a patient includes a tube for receiving the probe and selectively engaging the probe and the tissue, which tube has a cuff formed integrally therewith for carrying the probe.

In general, a method for engaging a sensor probe with the tissue of a patient includes the steps of engaging the tissue with the probe located within a cuff formed in a tube, and extending the tube over the tissue.

PREFERRED EMBODIMENT FOR CARRYING OUT THE INVENTION

Figure 1:
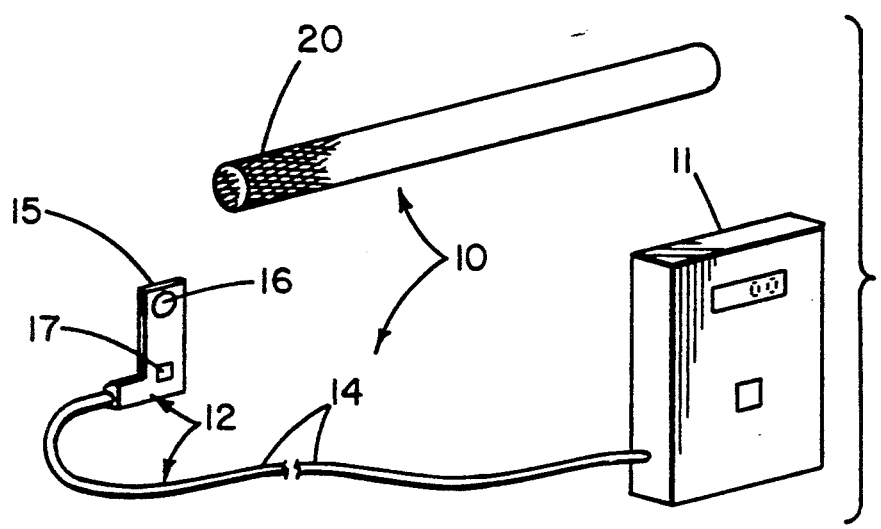
FIG. 1 is an elevation of the components of an exemplary device in accordance with the present invention and the exemplary oximeter in operative association therewith.

FIG. 1 presents in elevation the components of an exemplary device in accordance with the present invention, generally indicated by the numeral 10, and an exemplary oximeter 11 in operative association therewith, such as the Pulse Oximeter Model 8500 manufactured by Nonin Medical Incorporated of Plymouth, Minn. and described in U.S. Pat. No. 4,773,422. A conventional, non-invasive, electro-optical sensor probe 12 is electrically connected to oximeter 11 through cable 14. Probe 12 includes a flexible housing 15 carrying both a light source 16 for directing light through the tissue to be transilluminated, and a photosensor 17 for receiving the light directed through the tissue transilluminated by light source 16. Light source 16 and photosensor 17 are carried by housing 15 within wells 18, 19, respectively (best seen in FIGS. 2–5).

Device 10 includes a tube 20 for engaging probe 12 with the patient tissue of interest. Tube 20 is woven and may be made of any weavable material, such as plastic, nylon, metal or the like exhibiting the necessary flexibility and expandability explained hereinafter. One material found suitable is plastic monofilament and is presently readily available woven into tubes of various diameters.

Probe 12 is preferably attached to tube 20 prior to application to the tissue of interest. This may be done at the time of manufacture or just before application of device 10 to the tissue of interest, and may employ any technique as may occur to the skilled artisan.

Figure 2:
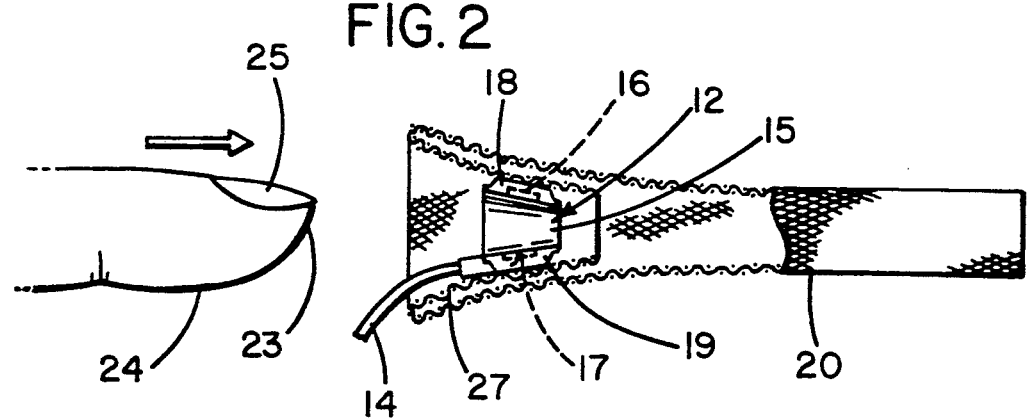
FIG. 2 is an elevation and partial sectional view of an exemplary device for engagement of an oximeter probe to the tissue at which the measurement is to be made, and illustrates commencement of the method of attaching the device to a fingertip.
Figure 3:
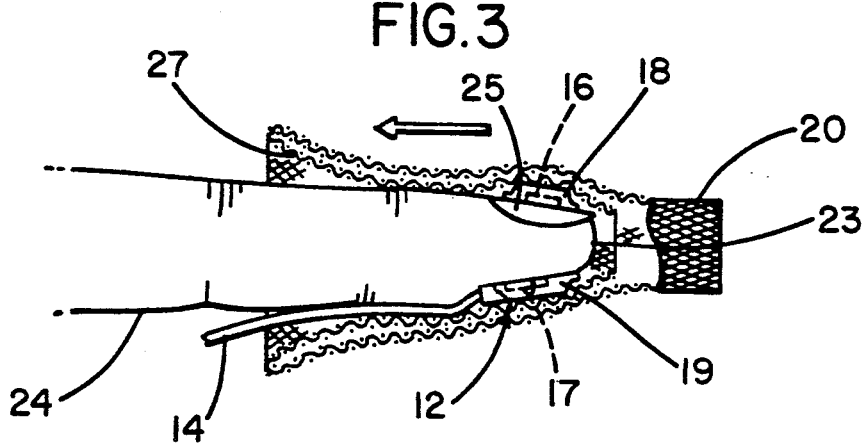
FIG. 3 is an elevation and partial sectional view of an exemplary device for engagement of an oximeter probe to the tissue at which the measurement is to be made, and illustrates an intermediate position during engagement of the device to a fingertip.
Figure 4:
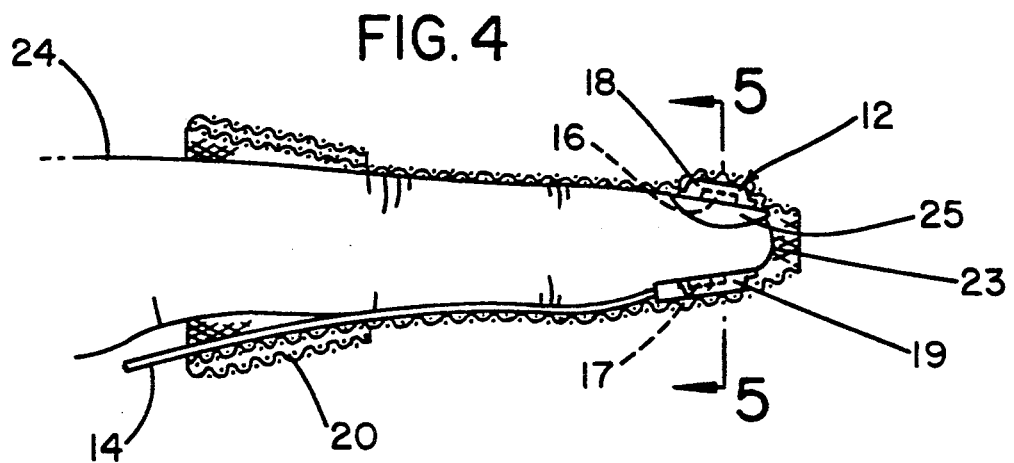
FIG. 4 is an elevation and partial sectional view of an exemplary device for engagement of an oximeter probe to the tissue at which the measurement is to be made, and illustrates the final position of the device when attached to a fingertip.
Figure 5:
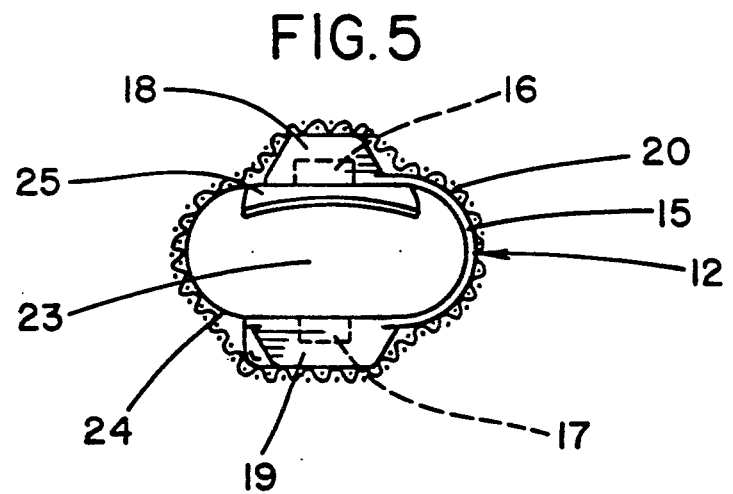
FIG. 5 is vertical section through the fingertip shown in FIG. 4 to which the probe has been attached.

Assembly of device 10 and its operation is straightforward and is best understood by reference to FIGS. 2, 3 and 4 which present an operational sequence of the engagement of probe 12 with an exemplary tissue of interest, the tip 23 of a human finger 24. As is known in the art, when a fingertip 23 is employed the most accurate measurement by oximeter 11 is achieved by positioning probe 12 so that it is wrapped around the tip 23 of finger 24, placing either light source 16 or photosensor 17 on fingernail 25 and the other opposite thereto on the underside of fingertip 23.

If probe 12 is not preattached to tube 20, this engaging positioning may be accomplished by first rolling one end of tube 20 into a cuff 27 sufficiently short to allow convenient insertion of probe 12 therein so that the center of probe 12 is at a distance from the end of tube 20 approximately equal to the distance from the patient's fingertip 23 to the center of fingernail 25. If probe 12 is preattached to tube 20, cuff 27 may be similarly preformed or formed at the time of use. Thereafter, fingertip 23 is gently inserted into cuff 27 until probe 12 is properly positioned and cuff 27 unrolled over the remainder of finger 24 to its base.

Among the advantages and other aspects of the present invention that should now be apparent to the skilled artisan, several should be noted. For example, as shown in FIG. 4, once unrolled, tube 20 secures a length of cable 14, minimizing motion artifact difficulties. Further, since device 10 may be repeatedly removed and reengaged at other tissue sites without damage to probe 12, device 10 may be installed at several tissue sites and finally positioned at the most desirable site. It will also be understood that device 10 may be readily applied to digits of all sizes by the simple expedient of selecting tube 20 to be of the appropriate diameter or other configuration and size. Tubes 20 of different shape and size may be color coded to facilitate expeditious selection of the correct size by the user and to make the location of probe 12 patient engagement more readily identifiable.

Also, while in the example given herein the shape and texture of both probe 12 (and in particular, wells 18, 19) and tube 20 should allow an interference fit to retain probe 12 in the desired position within tube 20, especially during insertion, the user may permit the use of tape, adhesive, mechanical interlock, or other means to assist in securing the same. Indeed, probe 12 may be manufactured with small mechanical interlocks that facilitate a positive connection with woven tube 20.

Inasmuch as the present invention is subject to variations, modifications and changes in detail, some of which have been expressly stated herein, it is intended that all matter described throughout this entire specification or shown in the accompanying drawings be interpreted as illustrative and not in a limiting sense. It should thus be evident that a device constructed and method performed according to the concept of the present invention, and reasonably equivalent thereto, will accomplish the objects of the present invention and otherwise substantially improve the art of engagement of an oximeter probe with the patient.

I claim:

1. A device comprising:
sensor probe means for engagement with a test surface; and tube means for receiving said probe means and selectively engaging said probe means and said test surface, said tube means having an end and including a cuff means for carrying said probe means, said cuff means formed integrally with said tube means by rolling said end of said tube means.

2. A device as set forth in claim 1, wherein said probe means is non-invasive and electro-optical said probe means engages blood-perfused tissue, and said tube means is substantially cylindrically shaped and made of woven material.

3. A device as set forth in claim 1, wherein said probe means is non-invasive and electro-optical, engages blood-perfused tissue, and said probe means includes a housing carrying a light source and a photosensor, said housing including interlock means for securing said probe means to said cuff means.

4. A device comprising:
means for engagement with blood-perfused tissue of a patient including a non-invasive, electro-optical sensor probe and a probe housing having separate wells carrying a light source and a photosensor;

and tube means for receiving said probe and selectively engaging said probe and said tissue, said tube means having an end and including a cuff means for carrying said probe, said cuff means formed integrally with said tube means by rolling said end of said tube means, said wells securing said probe to said cuff means by interference fit.

5. A method for engaging a sensor probe with the tissue of a patient including the steps of:
  engaging the tissue with the probe located within a cuff formed in a tube having an end by rolling said end of said tube; and,
  extending said tube over the tissue.

6. A method for engaging a non-invasive, electro-optical sensor probe with the blood-perfused tissue of a patient including the steps of:
  engaging the tissue with the probe located within a cuff formed in a tube; said step of engaging including the step of repeatedly engaging the tissue at multiple tissue sites to identify a preferred engagement location, and finally engaging the tissue with the probe at said preferred engagement location; and,
  extending said tube over the tissue.

7. A method for engaging a sensor probe with the tissue of a patient including the steps of:
  forming a cuff in a tube having an end by rolling said end of said tube;
  locating the probe within the cuff;
  engaging the tissue with the probe within the cuff; and,
  extending said tube over the tissue.

8. A method as set forth in claim 7, wherein the probe is non-invasive and electro-optical, the probe engages blood-perfused tissue, and said step of engaging includes the step of repeatedly engaging the tissue at multiple tissue sites to identify a preferred engagement location, and finally engaging the tissue with the probe at said preferred engagement location.

* * * * *

UNITED STATES PATENT AND TRADEMARK OFFICE
CERTIFICATE OF CORRECTION

PATENT NO. : 5,125,403
DATED : June 30, 1992
INVENTOR(S) : Joel B. Culp

It is certified that error appears in the above-identified patent and that said Letters Patent is hereby corrected as shown below:

Column 4, line 59, after "elctro-optical, " insert --said probe means --.

Signed and Sealed this

Tenth Day of August, 1993

Attest:

MICHAEL K. KIRK

Attesting Officer    Acting Commissioner of Patents and Trademarks